United States Patent [19]

Chou et al.

[11] 4,065,488

[45] Dec. 27, 1977

[54] PROCESS FOR PREPARING 1,4:3,6-DIANHYDRO-D-GLUCITOL 2-NITRATE

[75] Inventors: Chih H. Chou, Dollard des Ormeaux; Gordon S. Myers, Mount Royal, both of Canada

[73] Assignee: American Home Products Corporation, New York, N.Y.

[21] Appl. No.: 771,860

[22] Filed: Feb. 24, 1977

[51] Int. Cl.$^2$ .............................................. C07C 77/02
[52] U.S. Cl. ..................................... 260/467; 424/298
[58] Field of Search ......................... 260/467; 424/298

[56] References Cited

FOREIGN PATENT DOCUMENTS 984,899   3/1965   United Kingdom ................. 424/298

*Primary Examiner*—Leland A. Sebastian

[57] ABSTRACT

The following process for preparing 1,4:3,6-dianhydro-D-glucitol 2-nitrate is described: acylating 1,4:3,6-dianhydro-D-glucitol with 0.5 to 1.5 molar equivalents of acetic anhydride in the presence of an acid catalyst, nitrating the product so obtained with a mixture of nitric acid and acetic anhydride, hydrolyzing the product so obtained in the presence of an inorganic base and isolating 1,4:3,6-dianhydro-D-glucitol 2-nitrate. The 1,4:3,6-dianhydro-D-glucitol 2-nitrate is useful as a coronary vasodilator.

6 Claims, No Drawings

PROCESS FOR PREPARING 1,4:3,6-DIANHYDRO-D-GLUCITOL 2-NITRATE

BACKGROUND OF THE INVENTION a. Field of Invention

This invention relates to a novel and useful process for preparing 1,4:3,6-dianhydro-D-glucitol 2-nitrate.

b. Description of the Prior Art 1,4:3,6-Dianhydro-D-glucitol 2-nitrate, commonly called isosorbide-2-nitrate, has been established to be a useful compound having coronary vasodilator activity, see, for example, the report by R. L. Wendt, J. Pharmacol. Exp. Ther., 180, 732(1972).

1,4:3,6-Dianhydro-D-glucitol 2-nitrate has been prepared by the direct nitration of 1,4:3,6-dianhydro-D-glucitol by I. G. Csizmadia and L. D. Hayward, Photochem. Photobiol., 4, 657(1965). The 1,4:3,6-dianhydro-D-glucitol 2-nitrate is produced by the process of the latter reference as a minor constituent in a mixture of nitrates and has to be isolated from the mixture by column chromatography. The yield thereby obtained is very low and the method of isolation is time consuming and expensive so that use of this method as a commercial process is economically prohibitive. In addition, this prior art method also produces substantial quantities of 1,4:3,6-dianhydro-D-glucitol 2,5-dinitrate. This dinitrate, in contrast to the mononitrates, has potential explosive properties. In contradistintion, the process of this invention produces 1,4:3,6-dianhydro-D-glucitol 2-nitrate as the major component without any hazardous amounts of the dinitrate being formed. Moreover, the 1,4:3,6-dianhydro-D-glucitol 2-nitrate, being the principal reaction product in the process of this invention, is isolated directly in high purity by a simple crystallization of the crude reaction product from a suitable solvent. Thus, the process of this invention produces 1,4:3,6-dianhydro-D-glucitol 2-nitrate in an economically feasable method, without formation of any of the hazardous dinitrate, and the isolation and purification of the 2-nitrate by crystallization avoids the need for chromatography or other protracted and expensive purification procedures.

SUMMARY OF THE INVENTION

Herein is described a process for preparing 1,4:3,6-3,6-dianhydro-D-glucitol 2-nitrate which comprises the steps of:

a. acetylating 1,4:3,6-dianhydro-D-glucitol with 0.5 to 1.5 molar equivalents of acetic anhydride in the presence of an acid catalyst to obtain a mixture of 1,4:3,6-dianhydro-D-glucitol 5-acetate, 1,4:3,6-dianhydro-D-glucitol 2-acetate and 1,4:3,6-dianhydro-D-glucitol 2,5-diacetate;

b. nitrating the latter mixture with a mixture of nitric acid and acetic anhydride to obtain a mixture of 1,4:3,6-dianhydro-D-glucitol 5-acetate 2-nitrate, 1,4:3,6-dianhydro-D-glucitol 2-acetate 5-nitrate and 1,4:3,6-dianhydro-D-glucitol 2,5-diacetate; and c. hydrolyzing the latter mixture in the presence of an aqueous solution of an inorganic base and isolating 1,4:3,6-dianhydro-D-glucitol 2-nitrate.

DETAILS OF THE INVENTION

The systemic and coronary vascular effects of 1,4:3,6-dianhydro-D-glucitol 2-nitrate have been established by the report of R. L. Wendt, cited above. This report shows that 1,4:3,6-dianhydro-D-glucitol 2-nitrate reduces significantly systemic blood pressure and coronary resistance. Thus, the compound has utility as an anti-anginal agent.

When 1,4:3,6-dianhydro-D-glucitol 2-nitrate is used as a coronary vasodilator, it is used alone or in combination with pharmacologically acceptable carriers, the proportion of which is determined by the solubility and the chemical nature of the compound, chosen route of administration and standard biological practice. For example, it is administered parenterally by injection or orally, for instance, sublingually or gastrointestinally.

Therapeutic compositions containing the compound produced by the process of this invention are effective coronary vasodilators at dosages of 0.01 mg to 0.5 mg per kilogram of body weight when administered parenterally to a mammal. For administration to a mammal by parenteral injection, it is preferred to use the compound in solution in a sterile aqueous vehicle which may also contain other solutes such as buffers or preservatives, as well as sufficient quantities of pharmaceutically acceptable salts or of glucose to make the solution isotonic.

When the compound of this invention is employed as a coronary vasodilator in mammals, e.g. rats, dogs or humans, orally effective amounts of the compound are administered to the mammal, either alone or combined with pharmaceutically acceptable excipients in a dosage form, i.e. capsule or tablet, or the compound is administered orally in the form of solutions or suspensions. Therapeutic compositions containing the compound produced by the process of this invention are effective coronary vasodilators at oral dosages of 0.01 mg to 0.5 mg per kilogram of body weight when administered to a mammal. The latter dosage may be administered to the mammal one to five times a day, or as directed by a physician.

The tablet compositions contain the compound in admixture with non-toxic pharmaceutical excipients known to be suitable in the manufacture of tablets. Suitable pharmaceutical excipients are, for example, starch, milk sugar, certain types of clay and so forth. The tablets may be uncoated or they may be coated by known techniques so as to delay disintegration and absorption for sublingual or gastrointestinal use thereby provide a sustained action over a longer period.

The aqueous suspensions of the invention contain the compound in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one or more coloring agents, one or more flavoring agents and one or more sweetening agents.

Non-aqueous suspensions may be formulated by suspending the compound in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, a flavoring agent and an anti-oxidant.

The dosage of the compound will vary with the form of administration. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects, and preferably at a level that is in a range of from about 0.01 mg to about 2.5 mg per kilogram of body weight per day, although as aforementioned variations will occur. However, a dosage level that is in the range of from about 0.1 mg to about 1.0 mg per kilogram of body weight per day is most desirably employed in order to achieve effective results.

Process

The process of this invention is carried out in the following manner:

Acetic anhydride (0.5 to 1.5 molar equivalents, preferably 0.8 to 1.2 molar equivalents) is added over a period of 1 to 8 hours to a solution at 0° to 30° C, preferably 0° to 10° C, of 1,4:3,6-dianhydro-D-glucitol and an acid catalyst, preferably p-toluenesulfonic acid, hydrochloric acid, sulfuric acid, hydrobromic acid or phosphoric acid (0.001 to 0.010 molar equivalents, preferably 0.002 to 0.005 molar equivalents) in an inert solvent, for example, acetic acid or methylene chloride. Acetic acid is a preferred solvent. After completion of the addition, the reaction mixture is stirred at 5° to 30° C for 2 to 5 hours. The reaction mixture is concentrated, preferably under reduced pressure, to obtain a residue containing a mixture of 1,4:3,6-dianhydro-D-glucitol 2-acetate, 1,4:3,6-dianhydro-D-glucitol 5-acetate and 1,4:3,6-dianhydro-D-glucitol 2,5-diacetate.

The latter mixture contains amounts of unreacted 1,4:3,6-dianhydro-D-glucitol, which would lead to the formation of the potentially hazardous 1,4:3,6-dianhydro-D-glucitol 2,5-dinitrate if the mixture is subjected to the next step. 1,4:3,6-Dianhydro-D-glucitol is removed from the residue by extraction. In this instance, the residue is dissolved in an inert water-immiscible organic solvent, preferably methylene chloride, chloroform, trichloroethane, ethyl acetate, diethyl ether and the like. The resulting organic solution is extracted with water and/or brine to remove unreacted 1,4:3,6-dianhydro-D-glucitol and concentrated under reduced pressure to obtain a residue containing a mixture of 1,4:3,6-dianhydro-D-glucitol 2-acetate, 1,4:3,6-dianhydro-D-glucitol 5-acetate and 1,4:3,6-dianhydro-D-glucitol 2,5-diacetate.

A selective acetylation of 1,4:3,6-dianhydro-D-glucitol with acetic anhydride to obtain preferentially 1,4:3,6-dianhydro-D-glucitol 5-acetate has been described by K. W. Buck et al., Carbohydrate Res., 2, 122(1966).

Either one of the above residues containing the mixture of the 2-acetate, 5-acetate and 2,5-diacetate of 1,4:3,6-dianhydro-D-glucitol is nitrated. The preferred nitration method is to add slowly the residue over a period of 0.1 to 5 hours to a solution at −5° to 25° C, preferably 0° to 5° C, of one to 20 molar equivalents, preferably three to five molar equivalents, of acetic anhydride and one to ten molar equivalents, preferably one to two molar equivalents, of nitric acid. After the addition is completed, the reaction mixture is stirred for about 0.5 to 2 hours at −5° to 25° C, preferably 0° to 5° C, in order to complete the nitration. In this manner a solution containing a mixture of 1,4:3,6-dianhydro-D-glucitol 5-acetate 2-nitrate, 1,4:3,6-dianhydro-D-glucitol 2-acetate 5-nitrate and 1,4:3,6-dianhydro-D-glucitol 2,5-diacetate is obtained.

In the preferred embodiment of the process, the solution containing the mixture is subjected directly to selective alkaline hydrolysis to remove the acetate groups.

The latter selective alkaline hydrolysis is readily achieved by adjusting the above solution containing a mixture of 1,4:3,6-dianhydro-D-glucitol 5-acetate 2-nitrate, 1,4:3,6-dianhydro-D-glucitol 2-acetate 5-nitrate and 1,4:3,6-dianhydro-D-glucitol 2,5-diacetate with a sufficient quantity of an aqueous solution of an inorganic base until the reaction solution reaches pH 10 to 12 and maintaining the reaction solution at the latter pH until the acetate groups are hydrolyzed. The inorganic base selected for this hydrolysis must be capable of maintaining the reaction solution at pH 10 to 12. A suitable inorganic base can be selected from a hydroxide or carbonate of potassium or sodium.

In the preferred method of hydrolysis, the above reaction solution, after completion of nitration, is maintained at 0° to 30° C, preferably 0° to 10° C, and water (about 1 to 10 molar equivalents, preferably about 1.1 to 4 molar equivalents) is added. A 20 to 50% aqueous solution of an alkali metal hydroxide (preferably sodium or potassium hydroxide) is added until the reaction solution reaches pH 10.0 to 12.0. The alkaline reaction mixture is stirred at 20° to 30° C for 2 to 20 hours. Further additions of the aqueous alkali metal hydroxide solution may be mecessary to maintain the pH of the reaction mixture between 10.0 and 12.0. The aqueous alkaline reaction solution now contains a mixture of 1,4:3,6-dianhydro-D-glucitol 2-nitrate, 1,4:3,6-diahydro-D-glucitol 5-nitrate and 1,4:3,6-dianhydro-D-glucitol.

To facilitate the following extraction the latter aqueous alkaline reaction solution can be diluted with sufficient water and if required warmed to about 30° C to dissolve any solid inorganic salts. At this point, the solution may be extracted with a small volume, about 0.05 volume, of a non-polar organic first solvent, for example, benzene, toluene or hexane, or mixtures thereof, in order to remove any trace amounts of 1,4:3,6-anhydro-D-glucitol 2,5-dinitrate that may be present. It should be noted that the presence of trace amounts of the dinitrate does not represent an explosive hazard.

A surprisingly effective, and practical method of the isolation of 1,4:3,6-dianhydro-D-glucitol 2-nitrate comprises the following steps. The aqueous alkaline solution is extracted with an inert water-immiscible organic solvent, preferably by extracting three to ten times with 0.10 to 0.30 volume of an inert water-immiscible organic solvent more polar than the said first solvent. Suitable solvents for the purpose are diethyl ether, diisopropyl ether, ethyl acetate, methylene chloride, chloroform, trichlorothane and the like. The preferred solvents are the chlorinated hydrocarbon solvents, methylene chloride, chloroform or trichloroethane. In this manner, 1,4:3,6-dianhydro-D-glucitol remains in the aqueous alkaline solution, and the organic extract contains a mixture of the 2-nitrate and 5-nitrate of 1,4:3,6-dianhydro-D-glucitol. Concentration of the latter extract, preferably under reduced pressure, affords a residue containing a mixture of the 2-nitrate and 5-nitrate, in which the 2-nitrate is the major component and representing more than 65% of the weight of the residue. In other words, the ratio of the 2-nitrate to 5-nitrate in this residue is greater than 2 to 1, respectively. Unexpectedly, we have found that the mixture of the 2- nitrate and 5-nitrate in such a ratio permits the isolation of the pure 2-nitrate by direct crystallization of the residue. Accordingly, crystallization affords substantially pure (at least 90%, usually at least 98%) crystals of 1,4:3,6-dianhydro-D-glucitol 2-nitrate. Suitable solvents for this crystallization can be selected from methanol, ethanol, propanol, isopropanol, butanol, diethyl ether, diisopropyl ether ethyl acetate and the like, or mixtures thereof. Preferably the crystallization mixture is seeded with crystals of 1,4:3,6-dianhydro-D-glucitol 2-nitrate. The preferred solvent for the crystallization is isopropanol. If required the latter compound can be recrystallized to obtain crystals of 1,4:3,6-dianhydro-D-glucitol 2-nitrate having a purity of at least 99.8%.

The above described selective alkaline hydrolysis of an acetate group in the presence of a nitrate group is also applicable to the hydrolysis of pure 1,4:3,6-dianhydro-D-glucitol 5-acetate 2-nitrate. Thus, if required, 1,4:3,6-dianhydro-D-glucitol 5-acetate 2-nitrate can be separated from 1,4:3,6dianhydro-D-glucitol 2-acetate 5-nitrate (for instance by column chromatography and/or crystallization), hydrolyzed in the above described manner using an alkali metal hydroxide and crystallized to obtain substantially pure crystals of 1,4:3,6-dianhydro-D-glucitol 2-nitrate.

A nitration of the 2-acetate or 5-acetate of 1,4:3,6-dianhydro-D-glucitol has been described giving only general conditions in the Canadian Pat. No. 967,164, issued May 6, 1975.

The following examples illustrate further the process of this invention.

EXAMPLE 1

Acetic acid (25 l.) is added to 1,4:3,6-dihydro-D-glucitol (60 kg) followed by a slurry of p-toluenesulfonic acid (180 g) and acetic acid (500 ml). The mixture is cooled under nitrogen to −5° C and acetic anhydride (42 kg) is added over a period of 5 hours while the reaction mixture is maintained at 5° to 7° C. At the end of the addition, the resulting solution is stirred for 3 hours at room temperature. Sodium acetate (102 g) is added and the solution is concentrated under reduced pressure at 65° to 70° C until a syrupy liquid residue is obtained. The residue is diluted with methylene chloride (150 l.) and extracted with aqueous sodium chloride solution (25%, 3 × 30 l.) and then with water (15 l.) to remove unreacted 1,4:3,6-dianhydro-D-glucitol. Each aqueous sodium chloride extract is extracted with methylene chloride to remove dissolved acetates of 1,4:3,6-dianhydro-D-glucitol. The methylene chloride extracts and the above methylene chloride solution are combined and evaporated under reduced pressure to give a syrupy liquid residue (65.6 kg) containing a mixture of 1,4:3,6-dianhydro-D-glucitol 2-acetate, 1,4:3,6-dianhydro-D-glucitol 5-acetate and 1,4:3,6-dianhydro-D-glucitol 2,5-diacetate.

EXAMPLE 2

Nitric acid (70%, 36.9 kg) is slowly added over a period of 3 hours to acetic anhydride (110.4 kg) maintained at 2° C under nitrogen and after completion of addition the solution is cooled to 0° C. The syrupy liquid residue (65.6 kg, described in Example 1) is added over a period of 2 hours while the reaction mixture is maintained at 0° to 3° C. The reaction is stirred at 0° C for 1 hour and water (120 l.) is added over a period of 1 hour while maintaining a reaction temperature of 0° to 8° C. Aqueous sodium hydroxide solution (40%, 210 l.) is slowly added while maintaining a reaction temperature of 20° to 25° C until the reaction mixture reaches pH 10.5 to 11.5. The reaction mixture is stirred at 25° C for 18 hours and if necessary additional 40% sodium hydroxide solution is added in order to maintain pH 10.5 to 11.0. The reaction mixture is diluted to a volume of 600 l. with water and extracted with toluene (1 × 36 l. and 1 × 12 l.) to remove trace amounts of 1,4:3,6-dianhydro-D-glucitol 2,5-dinatrate which may be present. The toluene extracts are combined, diluted with heptane (24 l) and extracted with water (4 × 24 l.). The aqueous extracts are added to the 600 l. of the above aqueous phase. The combined aqueous phase is warmed to 27° C in order to dissolve any remaining solid inorganic salts, adjusted to pH 8 with 93% sulfuric acid (5 l) and extracted with methylene chloride (5 × 90 l.). The combined organic extract is washed with water (3 × 6 l.) and evaporated under reduced pressure. Isopropanol (145 l.) and a crystal of 1,4:3,6-dianhydro-D-glucitol 2-nitrate is added. The mixture is concentrated to 177 l. under reduced pressure and a solution temperature of −10° C is reached. Isopropanol (10 l.) is added and the mixture is stirred at −10° C for 2 hours. The mixture is filtered and the precipitate is washed with cold isopropanol (4 × 5 l.) and dried under reduced pressure at room temperature to give crystals of 1,4:3,6-dianhydro-D-glucitol 2-nitrate (mp 53.5° to 55.5° C, 18.9 kg, 99% purity as determined by thin layer chromatography using silica gel G plates which are eluted with chloroform-methanol 96:4 and developed by spraying with concentrated sulfuric acid followed by heating).

We claim:

1. A process for preparing 1,4:3,6-dianhydro-D-glucitol 2-nitrate which comprises the steps of:
   a. acetylating 1,4:3,6-dianhydro-D-glucitol with 0.5 to 1.5 molar equivalents of acetic anhydride in the presence of an acid catalyst to obtain a mixture of 1,4:3,6-dianhydro-D-glucitol 5-acetate, 1,4:3,6-dianhydro-D-glucitol 2-dianhydro-D-glucitol 2,5-diacetate;
   b. nitrating the latter mixture with a mixture of nitric acid and acetic anhydride to obtain a mixture of 1,4:3,6-dianhydro-D-glucitol 5-acetate 2-nitrate, 1,4:3,6-dianhydro-D-glucitol 2-acetate 5-nitrate and 1,4:3,6-dianhydro-D-glucitol 2,5-diacetate; and
   c. hydrolyzing the latter mixture in the presence an aqueous solution of an inorganic base to obtain a mixture of 1,4:3,6-dianhydro-D-glucitol 2-nitrate and 1,4:3,6-dianhydro-D-dlucitol 5-nitrate in a ratio greater than 2:1 and isolating 1,4:3,6-dianhydro-D-glucitol 2-nitrate.

2. The process as claimed in claim 1 wherein 1,4:3,6-dianhydro-D-glucitol 2-nitrate is prepared comprising the steps of:
   a. acetylating 1,4:3,6-dianhydro-D-glucitol with 0.5 to 1.5 molar equivalents of acetic anhydride in the presence of an acid catalyst, concentrating the latter solution to obtain a syrupy liquid residue, dissolving the residue in an inert water-immiscible organic solvent to obtain an organic solution, washing the latter organic solution with water and/or brine and evaporating the organic solution to obtain a residue containing a mixture of 1,4:3,6-dianhydro-D-glucitol 5-acetate, 1,4:3,6-dianhydro-D-glucitol 2-acetate and 1,4:3,6-dianhydro-D-glucitol 2,5-diacetate;
   b. nitrating the latter residue with a solution of nitric acid and acetic anhydride to obtain a solution containing a mixture of 1,4:3,6-dianhydro-D-glucitol 5-acetate 2-nitrate, 1,4:3,6-dianhydro-D-glucitol 2-acetate 5-acetate and 1,4:3,6-dianhydro-D-glucitol 2,5-diacetate; and c. hydrolyzing the latter mixture in the presence of an aqueous solution of an inorganic base to obtain an aqueous alkaline solution containing a mixture of 1,4:3,6-dianhydro-D-glucitol 2-nitrate, 1,4:3,6-dianhydro-D-glucitol 5-nitrate and 1,4:3,6-dianhydro-D-glucitol, extracting the latter aqueous alkaline solution with an inert water-immiscible organic solvent to obtain an arganic solution containing 1,4:3,6-dianhydro-D-glucitol 2-nitrate and 1,4:3,6-dianhydro-D-glucitol 5-nitrate in a ratio greater than 2:1, concentrating the latter organic solution to obtain a residue and crystallizing the latter residue to obtain crystals of 1,4:3,6-dianhydro-D-glucitol 2-nitrate.

3. The process as claimed in claim 1 wherein 1,4:3,6dianhydro-D-glucitol 2-nitrate is prepared comprising the steps of:

a. acetylating 1,4:3,6-dianhydro-D-glucitol with a solution at 0° to 30° C or 0.8 to 1.2 molar equivalents of acetic anhydride in acetic acid in the presence of 0.001 to 0.010 molar equivalents of an acid catalyst selected from p-toluenesulfonic acid, hydrochloric acid, sulfuric acid, hydrobromic acid and phosphoric acid, concentrating the reaction solution to obtain a syrupy liquid residue, dissolving the residue in an inert water-immiscible organic solvent to obtain an organic solution, washing the latter organic solution with water and/or brine and evaporating the organic solution to obtain a residue containing a mixture of 1,4:3,6-dianhydro-D-glucitol-5-acetate, 1,4:3,6-dianhydro-D-glucitol-2acetate and 1,4:3,6-dianhydro-D-glucitol-2,5-diacetate;

b. nitrating the latter residue with a solution at −5° to 5° C of three to five molar equivalents of acetic anhydride and one to two molar equivalents of nitric acid acid to obtain a solution containing a mixture of 1,4:3,6-dianhydro-D-glucitol 5-acetate 2-nitrate, 1,4:3,6-dianhydro-D-glucitol 2-acetate 5-nitrate and 1,4:3,6-dianhydro-D-glucitol 2,5-diacetate; and c. hydrolyzing the latter mixture at 0° to 30° C in the presence of an aqueous solution of an inorganic base selected from an hydroxide of potassium or sodium at pH 10.0 to 12.0 to obtain an aqueous alkaline solution containing a mixture of 1,4:3,6-dianhydro-D-glucitol 2-nitrate, 1,4:3,6-dianhydro-D-glucitol 5-nitrate and 1,4:3,6-dianhydro-D-glucitol, extracting the latter alkaline solution with an inert water-immiscible organic solvent to obtain an organic solution containing 1,4:3,6-dianhydro-D-glucitol 2-nitrate and 1,4:3,6-dianhydro-D-glucitol 5-nitrate in a ratio greater than 2:1, concentrating the latter organic solution to obtain a residue and crystallizing the latter residue to obtain substantially pure crystals of 1,4:3,6-dianhydro-D-glucitol 2-nitrate.

4. The process as claimed in Claim 3 wherein step (a) said inert water-immisicible organic solvent is selected from methylene chloride and chloroform.

5. The process as claimed in claim 3 wherein step (c) said inert water-immisicible organic solvent is selected from methylene chloride or chloroform.

6. The process as claimed in claim 3 wherein step (c) said residue is crystallized from isopropanol to obtain substantially pure crystals of 1,4:3,6-dianhydro-D-glucitol 2-nitrate.

* * * * *

UNITED STATES PATENT AND TRADEMARK OFFICE
CERTIFICATE OF CORRECTION

PATENT NO. : 4,065,488
DATED : December 27, 1977
INVENTOR(S) : Drs. Chih H. Chou and Gordon S. Myers It is certified that error appears in the above-identified patent and that said Letters Patent are hereby corrected as shown below:

Column 1, line 47, for "3,6-dianhydro-D-glucitol" read —dianhydro-D-glucitol—,

Column 6, line 39, Claim 1, for "2-dianhydro-D-glucitol 2,5-" read —2-acetate and 1,4:3,6-dianhydro-D-glucitol 2,5- —, Column 6, line 49, Claim 1, for "D-dlucitol" read — D-glucitol —, Column 7, line 12, Claim 2, for "arganic" read —organic—, Column 7, line 21, Claim 3, for "1,4:3,6dianhydro-D-glucitol" read —1,4:3,6-dianhydro-D-glucitol—, Column 7, line 24, Claim 3, for "or" read — of —

Column 8, line 1, Claim 3, for "2acetate" read — 2-acetate — and

Column 7, line 3, Claim 2, for "2-acetate" read —2-nitrate —.

Signed and Sealed this

Twenty-ninth Day of August 1978

[SEAL]

Attest:

RUTH C. MASON
Attesting Officer

DONALD W. BANNER
Commissioner of Patents and Trademarks